US009090978B2

(12) United States Patent
Beckett

(10) Patent No.: US 9,090,978 B2
(45) Date of Patent: Jul. 28, 2015

(54) HYDROGEN PRODUCTION

(71) Applicant: Unique Global Possibilities (Australia) Pty Ltd, Ulladulla, NSW (AU)

(72) Inventor: Russell Beckett, Mollymook Beach (AU)

(73) Assignee: Unique Global Possibilites (Australia) Pty Ltd, Ulladulla (AU)

( * ) Notice: Subject to any disclaimer, the term of this patent is extended or adjusted under 35 U.S.C. 154(b) by 12 days.

(21) Appl. No.: 13/926,408

(22) Filed: Jun. 25, 2013

(65) Prior Publication Data

US 2014/0080927 A1     Mar. 20, 2014

(30) Foreign Application Priority Data

Sep. 19, 2012   (AU) .................................. 2012904094

(51) Int. Cl.
*C25B 1/10* (2006.01)
*B01D 53/62* (2006.01)
*C10G 2/00* (2006.01)
*C25B 1/04* (2006.01)
*B01D 53/22* (2006.01)

(52) U.S. Cl.
CPC . *C25B 1/10* (2013.01); *B01D 53/62* (2013.01); *C10G 2/50* (2013.01); *C25B 1/04* (2013.01); *B01D 53/22* (2013.01); *B01D 2256/16* (2013.01); *Y02E 60/366* (2013.01); *Y02E 60/50* (2013.01)

(58) Field of Classification Search
CPC ............ C25B 1/10; C25B 1/04; Y02E 60/36; Y02E 60/366; Y02E 60/50; B01D 2256/16; B01D 53/22; B01D 53/62; C10G 2/50

USPC ........................................... 205/637; 518/704
See application file for complete search history.

(56) References Cited

U.S. PATENT DOCUMENTS

| | | | |
|---|---|---|---|
| 2008/0115500 A1* | 5/2008 | MacAdam et al. ............. 60/772 |
| 2008/0245660 A1* | 10/2008 | Little et al. .................... 204/242 |
| 2008/0318092 A1* | 12/2008 | Sridhar et al. .................. 429/13 |
| 2010/0193370 A1* | 8/2010 | Olah et al. ..................... 205/450 |
| 2010/0200419 A1* | 8/2010 | Gilliam et al. ................. 205/351 |
| 2010/0230293 A1* | 9/2010 | Gilliam et al. ................. 205/349 |
| 2012/0226080 A1 | 9/2012 | Meyer-Pittroff |
| 2013/0032488 A1* | 2/2013 | Tai et al. ....................... 205/412 |

FOREIGN PATENT DOCUMENTS

WO      2010149263 A1    12/2010

OTHER PUBLICATIONS

Pauling, Linus "Chapter 15: Oxidation-Reduction Reactions. Electrolysis." p. 512-550 (1970). General Chemistry (3rd Edition). Dover Publications.*
International Search Report and Written Opinion from counterpart PCT Application No. PCT/AU2013/001062 mailed on Oct. 21, 2013 (9 pages).

* cited by examiner

*Primary Examiner* — Jafar Parsa
*Assistant Examiner* — Amy C Bonaparte
(74) *Attorney, Agent, or Firm* — Wood, Herron & Evans, LLP

(57) ABSTRACT

The invention relates to a process for generating hydrogen. In this process an aqueous liquid is exposed to carbon dioxide and a current is passed through the aqueous liquid so as to generate hydrogen.

21 Claims, 4 Drawing Sheets

HYDROGEN PRODUCTION

FIELD

The invention relates to improvements in generation of hydrogen.

BACKGROUND

USA and Europe and other developed and developing countries face challenges in the areas of air pollution, public health, economic growth, energy security and national security as a result of overdependence on petroleum fuels. In January 2012, the Californian emissions trading scheme came into effect. This aims to reduce carbon dioxide emissions from the use of petroleum and other fossil fuels. In June 2012, the US Court of Appeals upheld the US Administration's set of clean car and fuel economy standards which aim to cut new car pollution, and petroleum use, in half by 2025.

A solution to the above problems is to develop a non-polluting, more secure and more sustainable transportation and energy economy utilising hydrogen. Indeed, this is recognised worldwide. Hydrogen is a high energy source with water as the non-polluting final combustion product.

At present, commercial hydrogen production relies mainly on the steam reformation of methane (natural gas). Over three quarters of the global production of hydrogen occurs using steam-methane reformation. In this process, steam and methane at high temperatures (about 1,000° C.) react to yield synthesis gas or syngas (a mixture of carbon monoxide and hydrogen). The carbon monoxide produced can be converted, by a subsequent water gas shift reaction, to carbon dioxide with the production of more hydrogen.

Commercial hydrogen production also occurs via the gasification of coal. In this process, steam and oxygen at high temperatures and pressures react with coal to yield syngas. Coal gasification is the oldest method of hydrogen production in both Europe and the USA.

Small commercial amounts of pure hydrogen are produced from the electrolysis of water. In this process, water is decomposed into hydrogen and oxygen using an electric current passed between two electrodes that are immersed in the water. Hydrogen is collected at the cathode and oxygen is collected at the anode.

The decomposition of water into hydrogen and oxygen by electrolysis at standard temperature and pressure is not favourable thermodynamically. Energy in the form of electricity or heat must be supplied. The reaction occurring at the anode can be represented by:

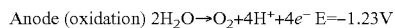

Anode (oxidation) $2H_2O \rightarrow O_2 + 4H^+ + 4e^-$ $E = -1.23V$

The reaction occurring at the cathode can be represented by:

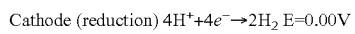

Cathode (reduction) $4H^+ + 4e^- \rightarrow 2H_2$ $E = 0.00V$

Pure water conducts electricity poorly. If an appropriate electrolyte at an appropriate concentration is added to water, the electrical conductivity of water increases considerably. Care must be exercised in the choosing of electrolytes so that competition does not occur between the electrolyte and water to gain electrons at the cathode (reduction of cation) and to give up electrons at the anode (oxidation of anion).

Other methods of hydrogen production that are less common include biomass gasification, the carbon black and hydrogen process, photoelectrolysis, thermal decomposition of water, and photobiological production.

The production of hydrogen from methane produces large amounts of carbon oxides and produces several other pollutants and toxic by-products. Some impurities, such as carbon monoxide, are poisonous to humans and can be detrimental to various systems that require hydrogen—particularly hydrogen fuel cells containing proton exchange membranes. These impurities have delayed the utilisation of hydrogen fuel cells in automobiles and public transport.

The production of hydrogen from the electrolysis of water results in the least contaminated hydrogen product. Some pollutants may arise if electrolytes are added to the water to facilitate the process or to increase the velocity of the process, or if other substances are present in the water. Pollutants may arise particularly at the anode with the oxidation of anions (anode mud, etc.). Some pollutants may occur at the cathode from reactions with protons and electrons and substances present in water (carbon compounds for example). Either damage to, or dissolution of, electrodes may occur and the replacement of electrodes results in substantial financial costs. However, in principle, the production of hydrogen by the electrolysis of water should minimise considerably the overall production of carbon dioxide, pollutants and toxic by-products compared to other methods of hydrogen production.

Hydrogen can be used as a fuel directly in an internal combustion engine. Some automobile companies produce automobiles that can combust either hydrogen or gasoline. Because of its relative purity, the hydrogen produced by the electrolysis of water can be utilised also in hydrogen fuel cells. In a hydrogen fuel cell, as with hydrogen combustion, water is the final product. Vehicles in cities that operate utilising either hydrogen fuel cells or hydrogen combustion produce negligible pollutants compared with vehicles combusting gasoline or methane or other fossil fuels. The large scale use of hydrogen, produced by electrolysis, either in fuel cells or in internal combustion engines of vehicles would diminish city air pollution very significantly.

In addition, those countries that import oil and petroleum fuels can utilise hydrogen as a general energy source and become economically less dependent on oil and petroleum fuel imports. Amongst a range of other advantages, a hydrogen economy is an economy that has energy security, and hence, national security. Hydrogen is not only the cleanest energy available but it has the highest energy content of all fuels on a weight basis. The energy content of hydrogen is about three times higher than gasoline, natural gas, and propane on a weight basis.

Hydrogen also is an essential component in the production of ammonia and a range of other compounds. The most important use of ammonia is as an agricultural fertiliser. Its importance arises also from its conversion into a wide range of nitrogen containing compounds. A source of uncontaminated hydrogen and ammonia is vital for a clean chemical and food industry.

At present, the cost of producing hydrogen from the electrolysis of water is many times the cost of producing hydrogen from methane. This high cost occurs because electrolysis in practice does not meet efficiencies that are possible in theory. Overpotentials are needed to overcome interactions at the electrode surface. Competing side reactions at the electrodes result in various products and pollutants and less than ideal Faradaic efficiency. In addition, much energy is lost as heat because of the difficulty in finding suitable electrodes—particularly anodes. The cost of hydrogen production from electrolysis is a linear function of the cost of electricity.

In the Sabatier reaction, carbon dioxide is converted to methane in the presence of hydrogen. For the Sabatier reaction to be economically viable, large amounts of hydrogen need to be produced at relatively low cost. The reaction has been studied extensively as a means of converting carbon dioxide emissions, from fossil fuel combustion, to methane. The methane produced is then capable of further combustion. NASA intends using the Sabatier reaction on the space station to produce water for consumption by astronauts and as a means of utilising atmospheric carbon dioxide on Mars to produce methane for fuel. Carbon dioxide recycling from power plants and other industries via the Sabatier reaction is recognised as a major means of capturing and utilising carbon dioxide. In this reaction, carbon dioxide and hydrogen react in the gaseous phase, which avoids expensive carbon dioxide capture, transport and geologic sequestration. The Sabatier reaction can be represented by:

$$CO_2 + 4H_2 \rightarrow CH_4 + 2H_2O$$

There is a need to decrease the cost of hydrogen production from the electrolysis of water. There is a need to produce hydrogen from the electrolysis of water without the production of pollutants or toxic by-products. There is a need to identify electrolytes or catalysts to facilitate the electrolytic process or to increase the rate of the electrolytic process, preferably without producing side reactions at the electrodes or pollutants or toxic by-products and without causing damage to electrodes. There is a need to decrease the power utilised in the electrolysis of water for hydrogen production. There is a need to decrease the reaction overpotential for the four electron oxidation of water to oxygen at the anode. There is a need to identify chemical catalysts and/or electro catalysts that can be utilised in the electrolysis of water to maximise the production of hydrogen per unit of electricity.

It is an object of the present invention to substantially overcome or at least ameliorate one or more of the above disadvantages. It is a further object to at least partially satisfy at least one of the above needs.

SUMMARY OF INVENTION

In a first aspect of the invention there is provided a process for generating hydrogen, said process comprising the steps of: a) exposing an aqueous liquid to carbon dioxide; and b) passing a current through the aqueous liquid so as to generate hydrogen.

The following options may be used in conjunction with the first aspect, either individually or in any suitable combination.

Step a) may comprise either passing a gas containing carbon dioxide through the aqueous liquid or exposing the surface of the aqueous liquid to a gas containing carbon dioxide or both. It may comprise exposing the aqueous liquid, optionally the surface of the aqueous liquid, to a gas containing carbon dioxide. The gas may have a higher concentration of carbon dioxide than is present in ambient air. In the gas, the carbon dioxide may have a partial pressure in said gas of at least about 0.01 atmospheres. The carbon dioxide may have a partial pressure in the gas of about 0.01 to about 100 atmospheres or of at least about 1 atmosphere. The gas may comprise at least about 95% carbon dioxide on a volume basis. The invention may comprise the step of providing the carbon dioxide. This step may involve providing a gas comprising carbon dioxide at a concentration higher than is present in ambient air, or at a concentration of at least about 500 ppm, or at least about 1000, 2000, 5000 or 10,000 ppm on a volume basis.

The gas may be released to the atmosphere following step a), optionally following step b), whereby the process is a process for reduction of emissions of carbon dioxide into the atmosphere. This reduction may be achieved by dissolving carbon dioxide in water or by production of bicarbonate at the anode or by reutilizing carbon dioxide to produce methane. The gas in step a) may be a waste gas from an industrial process. It may be a waste gas from power generation.

The aqueous liquid may comprise an electrolyte which is not derived from the carbon dioxide. It may comprise an electrolyte which is not aqueous carbon dioxide, a carbonate salt or a bicarbonate salt. The aqueous liquid prior to step a) may comprise an electrolyte. The aqueous liquid may be, or may be obtained from, potable water, non-potable water, waste water, storm water, reclaimed water, recycled water, sea water, ocean water, brackish water, saline water, brine, fresh water, stored water, surface water ground water or rain., or any combination of two or more of these.

The current may be applied under a voltage of about 0.1 to about 50V, or less than about 1.3V, or less than about 1V.

Step b) may in some instances be conducted at a voltage of about 0.4 to about 4V, whereby the process produces oxygen at the anode. The oxygen produced in this way may be used in Oxyfuel combustion. The combustion may be combustion of methane, coal or petroleum or of some other substance. Thus the oxygen may be combined with, or exposed to, a fuel and said fuel may then be combusted using Oxyfuel combustion.

In some embodiments no chlorine is produced. In particular, the aqueous liquid may comprise chloride ions (e.g. sea water or saline water) and the current may be passed at low voltages (e.g. less than 1.5 volts) whereby no chlorine gas is generated at the anode. The voltage may be sufficiently low that no chlorine is produced. In further embodiments no halogens ($X_2$, where X=F, Cl, Br or I) are produced. This may be due to the low voltage used or due to the absence of halide ions in the aqueous liquid or both.

The current may be less than about 20 amps, or less than about 1 amp, or less than about 0.01 amp. The current may be generated by green energy or from a renewable energy source. Suitable energy sources include photovoltaic cells or wind or tidal energy.

The aqueous liquid may have a pH of about 0 to about 9.

Step b) may comprise applying a voltage between a cathode and an anode. The cathode may be at least partially immersed in the aqueous liquid. The anode may be in electrical communication with the aqueous liquid. In some embodiments both the anode and the cathode are at least partially immersed in the aqueous liquid. At least one of the anode and the cathode may comprise a material selected from the group consisting of platinum, graphite, palladium, copper, zinc, silver, gold and mixtures thereof.

The hydrogen evolved in the process may be at least partially purified. The process may comprise the step of at least partially purifying the hydrogen generated in the process. The at least partially purifying may comprise passing the hydrogen through a gas separation membrane.

The process may additionally comprise reacting the hydrogen with carbon dioxide so as to produce methane and water.

The carbon dioxide used in the process may be derived from the combustion of a fossil fuel, for example coal, oil or natural gas. Alternatively it may be obtained from the production of liquid natural gas.

The process may be conducted in an electrolyser comprising a proton exchange membrane or a polymer electrolyte membrane (PEM).

In a particular embodiment of the invention there is provided a process for generating hydrogen, said process comprising the steps of: a) exposing an aqueous liquid of pH about 0 to about 9 to carbon dioxide; and b) passing a current of less than 1 amp under a voltage of less than 1.3V through the aqueous liquid so as to generate hydrogen, wherein step a) comprises either passing a gas containing carbon dioxide at a partial pressure of at least 0.01 atmospheres, optionally at least 1 atmosphere, through the aqueous liquid or exposing the surface of the aqueous liquid to a gas containing carbon dioxide at a partial pressure of at least 0.01 atmospheres, or both.

In another embodiment there is provided a process for generating hydrogen, said process comprising the steps of: a) exposing an aqueous liquid of pH about 0 to about 9 to a gas comprising carbon dioxide at a level of at least about 1000 ppm; and b) passing a current of less than 1 amp under a voltage of less than 1.3V through the aqueous liquid so as to generate hydrogen, wherein said gas is derived from the combustion of a fossil fuel, for example coal, oil or natural gas, or is obtained from the production of liquid natural gas or from power generation. This embodiment may represent a process for at least partially scrubbing carbon dioxide from said gas.

In another embodiment there is provided a process for generating hydrogen, said process comprising the steps of: a) exposing an aqueous liquid of pH about 0 to about 9 to a gas comprising carbon dioxide at a level of at least about 1000 ppm; and b) passing a current, optionally a current of less than about 1 amp, through the aqueous liquid under a voltage of about 0.4 to about 4V, so as to generate hydrogen and oxygen separately.

In a second aspect of the invention there is provided hydrogen produced by the first aspect of the invention. The hydrogen may be used for producing methane and water.

In a third aspect of the invention there is provided use of hydrogen produced by the first aspect of the invention for producing methane and water.

In a fourth aspect of the invention there is provided a method of producing methane and water comprising making hydrogen by the process of the first aspect and reacting the hydrogen with carbon dioxide so as to produce methane and water.

In a fifth aspect of the invention there is provided a method for increasing the rate of hydrogen production in electrolysis of an aqueous solution, said method comprising exposing the aqueous solution to carbon dioxide prior to and/or during said electrolysis.

The method may comprise exposing the aqueous solution to a gas comprising carbon dioxide. The gas may be a gas having a greater concentration of carbon dioxide than normal air. It may be a gas having a partial pressure of carbon dioxide of at least about 0.01 atmospheres, optionally of at least about 0.01 to about 100 atmospheres. It may be a gas having a carbon dioxide concentration of at least about 10% v/v, optionally of at least about 50% v/v, optionally of at least about 90% v/v.

In the method of the fifth aspect, the carbon dioxide may be, or may be derived from, and industrial waste gas. It may be, or may be derived from, combustion of a fuel or of a waste product, or may be, or may be derived from, some other industrial process. In this case the method may serve to scrub carbon dioxide from the gas so as to reduce carbon dioxide emissions from the industrial combustion or process.

There is also provided a method for increasing the rate of hydrogen production in electrolysis of an aqueous solution, said method comprising increasing the concentration of carbon dioxide in a gas to which the aqueous solution is exposed, said increasing occurring prior to and/or during said electrolysis.

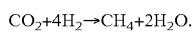

Figure 1:
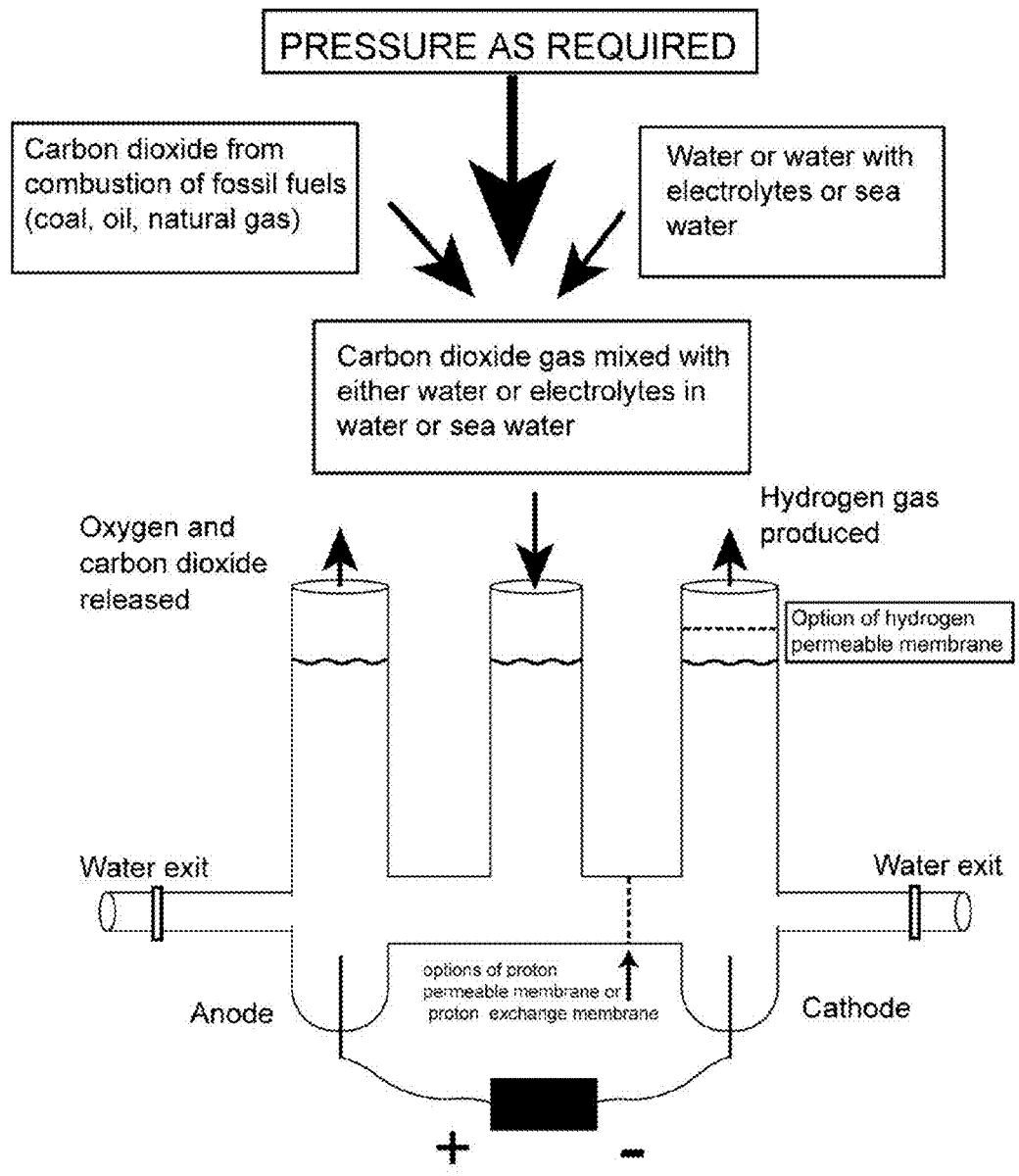
FIG. 1 is a diagramatic representation of a modified Hoffman apparatus with platinum electrodes apparatus used in the Examples.

$$CO_2 + 4H_2 \rightarrow CH_4 + 2H_2O.$$

DESCRIPTION OF EMBODIMENTS

The present invention provides a process for generating hydrogen, said process comprising the steps of: a) exposing an aqueous liquid to carbon dioxide; and b) passing a current through the aqueous liquid so as to generate hydrogen. The inventor has surprisingly found that more hydrogen may be produced, and/or hydrogen may be produced at a greater rate, by hydrolysis of water in the presence of carbon dioxide than in its absence. More particularly, an increase in hydrogen production from electrolysis of water is observed on increasing the concentration of carbon dioxide and/or of carbon dioxide derived species in the water. In particular, more hydrogen may be produced with lower power in the presence of carbon dioxide under pressure than is achievable at present. The present process therefore may be such that the hydrogen is produced in greater amount, and/or at a greater rate, than would be produced using the same conditions of electrolysis but without the step of exposing the aqueous liquid to carbon dioxide. It may generate more hydrogen, and/or generate hydrogen at a greater rate, than standard electrolysis of the aqueous liquid, all other conditions being equal. The increase in hydrogen generation and/or in rate may be at least about 5%, or at least about 10, 15, 20, 25, 50, 75 or 100%. Under some conditions it may be higher than this, e.g. at least about 1.5 fold, or 2, 3, 4, 5, 10, 20, 50 or 100 fold.

Step a) may refer to any suitable method for raising the concentration of carbon dioxide related species (carbon dioxide, carbonate, bicarbonate) in the aqueous liquid by use of carbon dioxide gas. Suitable methods include passing a gas containing carbon dioxide through the aqueous liquid and exposing the surface of the aqueous liquid to a gas containing carbon dioxide. A further suitable method is to expose the aqueous liquid to solid carbon dioxide. As the carbon dioxide sublimes (i.e. transforms from a solid directly to a gas) within the aqueous liquid, this results in exposure of the liquid to the sublimed (i.e. gaseous) carbon dioxide. It also results in cooling of the aqueous liquid, thereby increasing the solubility of the carbon dioxide in the liquid (as described elsewhere herein). In this instance, the solid carbon dioxide may be added in a single amount or may be added intermittently over time. For example it may be added repeatedly as soon as the previous amount has completely sublimed and/or dissolved.

The step of exposing may be for sufficient time to reach an equilibrium concentration of carbon dioxide in the aqueous liquid. This may be for at least 1 minute, or for at least 2, 3, 4, 5 or 10 minutes, or for about 1 to about 10 minutes, or about 1 to 5, 1 to 2 or 5 to 10 minutes, e.g. for about 1, 2, 3, 4, 5, 6, 7, 8, 9 or 10 minutes. In some cases it may be for less than 1 minute, or may be for more than 10 minutes. The exposing may be ceased before step b) or may be continued throughout step b) or may be conducted concurrently or at least partially concurrently with step b).

The gas containing carbon dioxide may have a higher concentration of carbon dioxide than that in normal air. It may comprise between about 0.01 and 100% carbon dioxide on a volume basis, or about 0.1 to 100, 1 to about 100, 10 to 100, 50 to 100, 80 to 100, 95 to 100, 0.01 to 50, 0.01 to 10, 0.01 to 1, 0.01 to 0.1, 0.1 to 50, 0.1 to 10, 0.1 to 1, 1 to 50, 1 to 10, 10 to 50, 50 to 95 or 80 to 95%, e.g. about 0.01, 0.02, 0.05, 0.1, 0.2, 0.5, 1, 2, 3, 4, 5, 10, 15, 20, 25, 30, 35, 40, 45, 50, 55, 60, 65, 70, 75, 80, 85, 90, 95 or 100% on a volume basis. The partial pressure of carbon dioxide in the gas may be at least about 0.01 atmospheres, or at least about 0.02, 0.05, 0.1, 0.2 0.5, 1, 2, 3, 4, 5, 10, 20, 30, 40, 50, 60, 70, 80, 90 or 100 atmospheres, or about 1 to about 100, 10 to 100, 50 to 100, 80 to 100, 95 to 100, 0.01 to 50, 0.01 to 10, 0.01 to 1, 0.01 to 0.1, 0.1 to 50, 0.1 to 10, 0.1 to 1, 1 to 50, 1 to 10, 10 to 50, 50 to 95 or 80 to 95 atmospheres, e.g. about 0.01, 0.02, 0.05, 0.1, 0.2, 0.5, 1, 2, 3, 4, 5, 10, 15, 20, 25, 30, 35, 40, 45, 50, 55, 60, 65, 70, 75, 80, 85, 90, 95 or 100 atmospheres. The total pressure of the gas may be about 1 atmosphere, or may be about 1 to about 100 atmospheres, or about 1 to 50, 1 to 20, 1 to 10, 1 to 5, 2 to 100, 5 to 100, 10 to 100, 50 to 100, 10 to 50 or 10 to 20 atmospheres, e.g. about 1, 2, 3, 4, 5, 10, 15, 20, 25, 30, 35, 40, 45, 50, 60, 70, 80, 90 or 100 atmospheres. Step a) may be sufficient to raise the concentration of carbon dioxide related species (as defined above) in the aqueous liquid by a factor of at least about 50% or at least about 100%, or by at least 2, 3, 4, 5, 10, 20, 50, 100, 200, 500 or 1000 fold. It may be sufficient to raise the concentration of carbon dioxide related species (as defined above) in the aqueous liquid by the above stated factor above the equilibrium concentration of carbon dioxide of the aqueous liquid in contact with normal air. In the event that the gas containing carbon dioxide is not 100% carbon dioxide, the carbon dioxide may be mixed with one or more other gases and/or vapours. These are preferably unreactive under the conditions of the process. Suitable gases and/or vapours include, but are not limited to, nitrogen, argon, helium, carbon monoxide and water vapour.

In the event that step a) comprises passing the gas through the aqueous liquid, this may comprise bubbling the gas therethrough. This may be for example through a frit or other dispersal device so as to reduce bubble size and/or increase bubble surface area. This may serve to accelerate equilibration with the aqueous liquid or to reach saturation of the liquid with carbon dioxide more rapidly. In some instances the step of passing the gas through the aqueous liquid may be such that the gas remains remote from the cathode. This may prevent the gas from mixing with the hydrogen evolved at the cathode. In some instances, as described elsewhere herein, the cathode is disposed in a cathode chamber and the anode in an anode chamber. Where these two chambers are separated, they must be electrically coupled so as to allow ions to travel between them. The electrical coupling may be such that it prevents passage of carbon dioxide gas. In this case the carbon dioxide containing gas may be passed through the aqueous liquid in the anode chamber so as to prevent it mixing with the evolved hydrogen at the cathode.

In a particular embodiment therefore, step a) of the process comprises exposing the surface of the aqueous liquid to an atmosphere of about 1 atmosphere, or of about 1 to about 20 atmospheres, of a gas comprising at least about 90% carbon dioxide on a mole or volume basis. In another particular embodiment, the process comprises passing a current through an aqueous liquid so as to generate hydrogen, the surface of said aqueous liquid being exposed to an atmosphere of about 1 atmosphere, or of about 1 to about 20 atmospheres, of a gas comprising at least about 90% carbon dioxide on a mole or volume basis. In a further particular embodiment, the process comprises passing a current through an aqueous liquid so as to generate hydrogen, whilst passing a gas comprising at least about 90% carbon dioxide on a mole or volume basis through said aqueous liquid. In a further particular embodiment, the process comprises passing a current through an aqueous liquid so as to generate hydrogen, the surface of said aqueous liquid being exposed to an atmosphere having a partial pressure of carbon dioxide of at least about 0.1 atmospheres, or at least about 1 atmosphere. In a further particular embodiment, the process comprises passing a current through an aqueous liquid so as to generate hydrogen, whilst passing a gas having a partial pressure of carbon dioxide of at least about 0.1 atmospheres, or at least about 1 atmosphere, through said aqueous liquid.

The aqueous liquid may comprise an electrolyte which is not derived from the carbon dioxide. This additional electrolyte may be an ionic salt. It may be a sodium salt, a potassium salt, a magnesium salt, a calcium salt, a chloride salt, a bromide salt, a sulfate salt, a nitrate salt or any suitable combination of these, or may be some other type of salt and/or other metallic and/or non-metallic material. The aqueous liquid may be, or may be obtained from, sea water or ocean water (typically about 3.5 percent salt), brackish water (typically about 0.05 to 3.5 percent salt), saline water (typically about 3.5 to 5 percent salt), or brine (typically more than 5 percent salt) or other suitable aqueous liquid. The concentration of the additional electrolyte may be about 0.05 to about 10% on a w/v basis in the aqueous liquid, or may be about 0.05 to 5, 0.05 to 1, 0.05 to 0.5, 0.05 to 0.1, 0.1 to 10, 1 to 10, 5 to 10, 0.1 to 1, 1 to 5, 2 to 5, 1 to 3 or 3 to 5%, e.g. about 0.05, 0.1, 0.5, 1, 1.5, 2, 2.5, 3, 3.5, 4, 4.5, 5, 6, 7, 8, 9 or 10% w/v. In some instances the aqueous liquid has no electrolyte other than an electrolyte derived from the carbon dioxide. The aqueous liquid may have no organic solvent mixed therewith, or may in some instances have a water miscible organic solvent, e.g. methanol, ethanol etc. Typically the concentration of the organic solvent, if present, will be less than about 10% v/v, or less than about 5, 1, 0.5 or 0.1% v/v.

The aqueous liquid may be agitated, e.g. shaken, stirred, swirled, sonicated or otherwise agitated during the passing of the current and/or during the step of exposing the aqueous liquid to carbon dioxide. This may for example be achieved by means of a stirrer or sonicator probe within the aqueous liquid. It may be facilitated by the presence of baffles or other barriers in the aqueous liquid, i.e. in the chamber in which the aqueous liquid is located. In one embodiment of the invention, the aqueous liquid is exposed to carbon dioxide (by any of the various methods described elsewhere herein) in an exposure chamber and then passes to a separate electrolysis chamber in which current is passed through the liquid so as to generate hydrogen. The electrolysis chamber may be a flow cell whereby the carbon dioxide exposed liquid flows through either intermittently or continuously. The liquid flowing out of the electrolysis chamber may be passed to waste or may be recycled through the exposure chamber where it may be re-exposed to carbon dioxide. Thus an apparatus for conducting the present invention may in one embodiment comprise a flow through electrolysis chamber coupled to an exposure chamber and having an anode and a cathode therein. A pump may be provided to cause the liquid to pass from the exposure chamber to the electrolysis chamber. The apparatus may also have a return line to return the aqueous liquid from the electrolysis chamber to the exposure chamber, or may have a waste line to pass the aqueous liquid from the electrolysis chamber to waste. In this embodiment, the electrolysis chamber may be as described elsewhere herein. It may comprise a single chamber having an anode and a cathode therein, or may comprise electrically coupled separate anode and cathode chambers. The exposure chamber may comprise a gas bubbler, frit or other dispersion device for passing a gas containing carbon dioxide (optionally mixed with one or more other gases, as described elsewhere herein) through the aqueous liquid, or may comprise a system for exposing the surface of the aqueous liquid to a gas containing carbon dioxide, or may comprise both of these.

The current may be applied under a voltage of about 0.1 to about 50V, or about 0.1 to 20, 0.1 to 10, 0.1 to 5, 0.1 to 2, 0.1 to 1.3, 0.1 to 1, 0.1 to 0.5, 0.5 to 1, 0.5 to 1.3, 0.5 to 2, 0.5 to 5, 0.5 to 10, 0.5 to 20, 0.4 to 4, 1 to 4, 2 to 4, 1 to 10, 1 to 5, 1 to 2 or 1 to 1.3V, e.g. about 0.1, 0.2, 0.3, 0.4, 0.5, 0.6, 0.7, 0.8, 0.9, 1, 1.1, 1.2, 1, 3, 1.4, 1.5, 2, 2.5, 3, 3.5, 4, 4.5, 5, 6, 7, 8, 9, 10, 15, 20, 25, 30, 35, 40, 45 or 50V. The applied voltage may be less than about 50V, or less than about 40, 30, 20, 10, 5, 4, 3, 2, 1.3, 1.23, 1 or 0.5V. It may be sufficiently low that, if the aqueous liquid contains chloride, no chlorine is produced at the anode. It may be sufficiently low that no oxygen is produced at the anode. Alternatively it may be sufficient for oxygen to be produced at the anode.

The current may be less than about 20 amps, or less than about 19, 18, 17, 16, 15, 14, 13, 12, 11, 10, 9, 8, 7, 6, 5, 4, 3, 2 or 1 amp, or less than about 0.5, 0.2, 0.1, 0.05, 0.02 or 0.01 amp. The current may be about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9 or 1 amp. The current may be about 1 amp, or about 2, 3, 4, 5, 6, 7. 8, 9, 10, 11, 12, 13, 14, 15, 16, 17, 18, 19 or 20 amps. The current may be generated by photovoltaic cells or by wind or tidal forces or by some other renewable or green energy source, e.g. falling water, co-generation, or energy obtained from biomass, natural gas or coal.

The current may be passed through the aqueous liquid at a power of less than about 100 W, or less than about 50, 20, 10, 5, 2, 1.5, 1, 0.5, 0.2 or 0.1 W, or of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 60, 70, 80, 90 or 100 W.

Step b) may in some instances be conducted at a voltage of about 0.4 to about 4V, so as to produce oxygen at the anode. The oxygen produced in this way may be used in Oxyfuel combustion. Oxyfuel combustion involves combustion of a fuel in an atmosphere having an oxygen concentration higher than that of ambient air rather than in ambient air, e.g. in an oxygen-enriched air atmosphere. The oxygen in the atmosphere in which the Oxyfuel combustion is conducted in the present instance may be for example at least about 30% by volume, or at least about 40, 50, 60, 70, 80, 90, 95, 96, 97, 98 or 99% by volume (excluding any gaseous fuel present). Thus if a solid fuel is used, the oxygen concentration may be as described. If however a gaseous or vapour phase fuel is used, the concentration of oxygen may be as described accounting for the concentration of the fuel. For example if a gaseous phase containing 10% by volume methane were used, the concentration of oxygen may be at least about 27% (i.e. 30% of the remaining 90% after methane is discounted) by volume. An advantage of Oxyfuel combustion is that the production of nitrogenous by-products is suppressed or eliminated. The nitrogen in the atmosphere in which the Oxyfuel combustion is conducted may be for example less than about 70% by volume, or less than about 60, 50, 40, 30, 20, 10, 5, 2 or 1%.

In order to achieve this, the oxygen may be purified prior to use in the Oxyfuel combustion. This may be for example by means of selective condensation of liquid gases followed by revaporisation, or may be by means of a selective gas membrane or may be by some other method. The oxygen from the present process, either after purification or without purification, may be mixed with a second gas, e.g. air, recycled flue gas etc. before being used as an atmosphere for the Oxyfuel combustion.

The aqueous liquid used in the process of the present invention may have a pH of about 0 to about 9, or about 0 to 8, 0 to 7, 0 to 6, 0 to 5, 0 to 4, 0 to 3, 0 to 2, 0 to 1, 1 to 9, 1 to 7, 1 to 5, 1 to 3, 3 to 9, 3 to 7, 3 to 5, 5 to 7, 7 to 9 or 6 to 8, e.g. about 0, 1, 2, 3, 4, 5, 6, 7, 8 or 9. This pH may be either as measured prior to step a) or as measured during step b). It may have a temperature of between 0 and 100° C., or 0 to 50, 0 to 20, 0 to 10, 10 to 100, 20 to 100, 50 to 100, 10 to 20, 20 to 50 or 20 to 30° C., e.g. about 0, 5, 10, 15, 20, 25, 30, 40, 50, 60, 70, 80, 90 or 100° C. It may have a subambient temperature. It may have a temperature of less than about 25° C., or less than about 20, 15, 10 or 5° C. This may serve to increase the solubility of the carbon dioxide in the aqueous liquid. This temperature may apply either during step a) or step b) or both. The process may comprise cooling the aqueous liquid. This may be done before and/or during either step a) or step b) or both. In some instances the cooling may be effected by means of solid carbon dioxide ("dry ice"). If sufficient solid carbon dioxide is used, excessive freezing of the aqueous liquid may occur, resulting in a loss of efficiency of the process. In such instances, heating may be applied so as to at least partially remelt the aquous liquid.

The process, in particular step b) of the process, may be conducted in any suitable apparatus for electrolysis of an aqueous liquid. Suitable apparatuses are well known to those skilled in the art. In one embodiment the apparatus comprises a proton exchange membrane or a polymer electrolyte membrane (PEM). This membrane may be used to separate the two half cells of the apparatus.

Step b) of the process may comprise applying a voltage between a cathode and an anode. Suitable materials for the two electrodes include (independently) platinum, graphite, palladium, copper, zinc, silver, gold and mixtures thereof, however the skilled worker will readily appreciate that other suitable electrode materials may also be used. Commonly both electrodes are at least partially immersed in the aqueous liquid, however in some instances the anode may be in electrical communication with the cathode without being immersed in the same body of aqueous liquid, e.g. by means of an ion bridge. The anode may be immersed in an aqueous liquid in an anode chamber and the cathode may be immersed in an aqueous liquid in a cathode chamber. The two aqueous liquids may each, independently, be as described earlier for "the" aqueous liquid (in which case they may be the same or may be different), or one or the other may be as so described and the other may be different. If the anode chamber is separate from the cathode chamber, the aqueous liquid in the cathode chamber or in the anode chamber or in both may be exposed to the carbon dioxide. If present, the anode chamber and the cathode chamber may be coupled by means of an ion bridge, an ion permeable membrane or by some other means for electrically coupling the chambers.

The hydrogen evolved in the process may be at least partially purified. This may for example be accomplished by passing through a gas separation membrane. Suitable membranes include dense polymer membranes, ceramic membranes, dense metallic membranes (e.g. Pd—Cu membranes) and porous carbon membranes.

Figure 4:
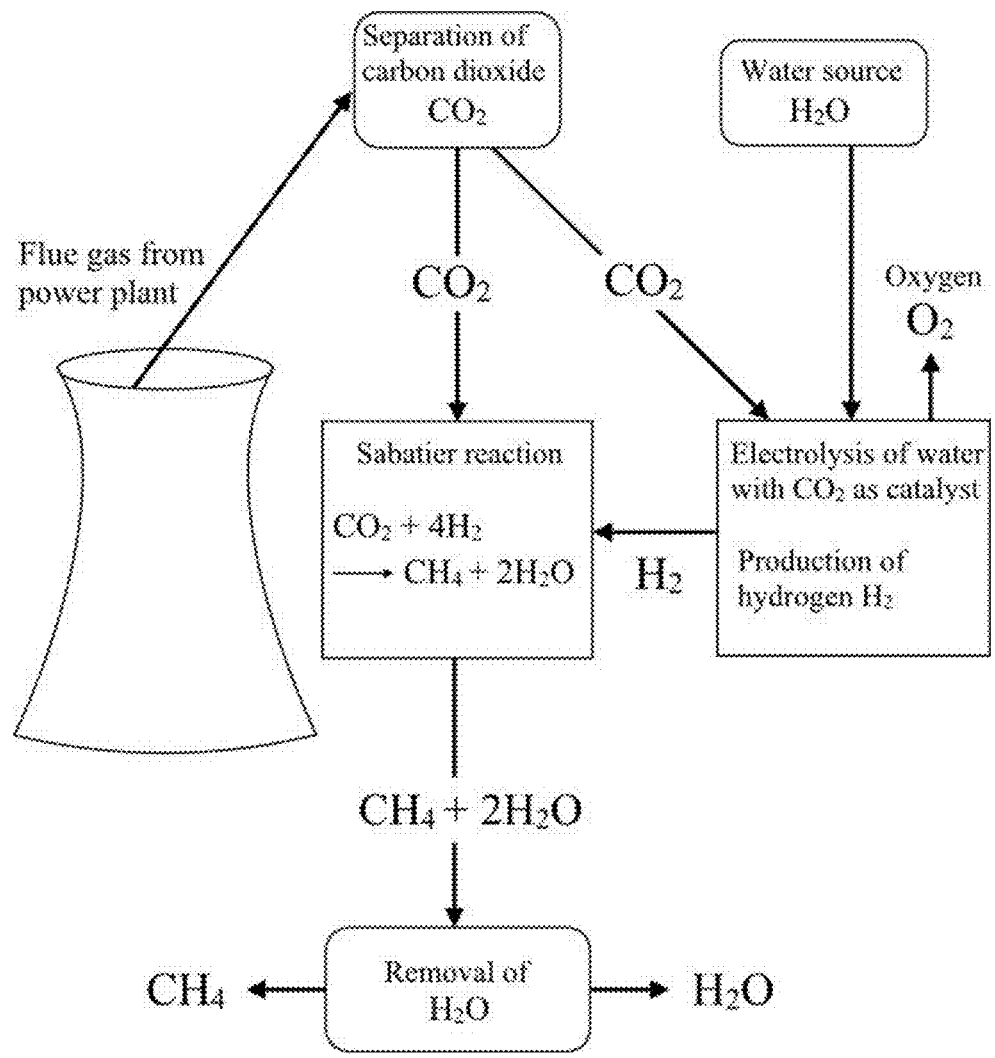
FIG. 4 shows a diagrammatic representation of the utilisation of hydrogen for the Sabatier reaction in recycling of carbon dioxide from power plant emissions.

The process may additionally comprise reacting the hydrogen with carbon dioxide so as to produce methane and water. This may for example be accomplished by means of the Sabatier reaction. This is illustrated diagrammatically in FIG. 4. For the Sabatier reaction to be economically viable, large amounts of hydrogen need to be produced at relatively low cost. Carbon dioxide recycling from power plants and other industries via the Sabatier reaction is recognised as a major means of capturing and utilising carbon dioxide. The reaction between carbon dioxide and hydrogen takes place in the gaseous phase which avoids expensive carbon dioxide capture, transport and geologic sequestration. The Sabatier reaction can be represented by:

$$CO_2 + 4H_2 \rightarrow CH_4 + 2H_2O$$

The hydrogen may alternatively be used as a fuel, e.g. in combustion to generate heat energy or in a hydrogen fuel cell.

An overall industrial scheme therefore may be as follows. Electrolysis of water according to the process of the present invention, commonly at low voltage (e.g. below 1.0V), generates hydrogen, which may be used in the Sabatier reaction (described above). Water produced in the Sabatier reaction may be recycled to the electrolysis chamber. Methane produced in the Sabatier reaction may be combusted, e.g. in an Oxyfuel reaction or simply in normal atmosphere, to generate energy. The carbon dioxide generated by this methane combustion may be separated from other combustion products and used either in the Sabatier reaction or in the electrolysis chamber (or both). If the electrolysis is conducted at higher voltage (i.e. above 1.0V), oxygen is generated in addition to hydrogen. This may be used in the Oxyfuel combustion of the methane generated from the Sabatier reaction, with the hydrogen being used as described above.

Aspects of the invention may therefore include one or more of the following:
a. Utilising a range of carbon dioxide pressures, e.g. from 0.01 atmospheres to 100 atmospheres.
b. Utilising a range of water temperatures, e.g. from 0 to 100° C.
c. Utilising a range of pH values, e.g. from pH=0 to pH=9.
d. Utilising a range of voltages between the electrodes, e.g. from 0.1 volts to 50 volts.
e. Utilising a range of electrode materials, e.g. platinum, graphite, palladium, copper, zinc, silver, gold and other metallic and non-metallic materials.
f. Utilising a range of electrolyte solutions or solutes in water, e.g. sodium chloride and other metal and non-metal salts.
g. Utilising sea water or ocean water (3.5 percent salt), brackish water (0.05 to 3.5 percent salt), saline water (3.5 to 5 percent salt), or brine (more than 5 percent salt) as an electrolyte.
h. Utilising diluted or filtered sea water or ocean water or brackish water or saline water or brine as an electrolyte.
i. Utilising a hydrogen separation cell or hydrogen permeable membrane to obtain the separation of hydrogen, for collection, from carbon dioxide and other gases.

Carbon dioxide dissolves to some extent in water at normal atmospheric pressure. At a gas pressure of one atmosphere (Standard Temperature and Pressure Dry—STPD) approximately 1.5 liters of carbon dioxide gas dissolves in 1 liter of cold water at 5° C. and 0.5 liters of carbon dioxide gas dissolves in 1 liter of warm water at 30° C. Accordingly, the concentration of carbon dioxide (optionally of carbon dioxide plus bicarbonate ion plus carbonate ion) during step b) of the present process may be at least about 0.1 liters (equivalent of carbon dioxide for carbonate and bicarbonate) per liter of water, or at least about 0.2, 0.3, 0.4, 0.5, 0.75, 1, 1.25 or 1.5 liters per liter of water, or about 0.1 to about 1.5, 0.1 to 1, 0.1 to 0.5, 0.5 to 1.5, 1 to 1.5 or 0.5 to 1 liters per liter of water, e.g. about 0.1, 0.2, 0.3, 0.4, 0.5, 0.75, 1, 1.25 or 1.5 liters per liter of water, depending on the temperature of the water. The inventor has found that under increasing pressure the concentration of carbon dioxide increases in water.

Water is a polar molecule with a dipole moment of 1.85 Debyes. Carbon dioxide does not possess a dipole moment but has a polarizability of $2.63 \times 10^{-24}$ cm$^3$. Carbon dioxide can be seen as a linear resonance. When carbon dioxide is dissolved in water, the slight negative charge on the oxygen atom of the water molecule attracts the slight positive charge on the carbon atom of carbon dioxide. It is thought that the product of this interaction is a proton ($H^+$) and a bicarbonate ion ($HCO_3^-$).

The inventor has found that under increasing pressure and/or increasing carbon dioxide concentration, the concentrations of protons and bicarbonate ions increase. It is possible to achieve a proton and bicarbonate ion concentration of more than $10^{-1}$ moles per liter by further increasing the contact between carbon dioxide molecules and water molecules either by further increasing pressure or by utilising appropriate mixing and mechanical baffles. That is, it is possible to reach a pH value less than pH=1. In biology and human physiology, the enzyme carbonic anhydrase produces sufficient proton concentrations from carbon dioxide and water to achieve pH values between pH 2 and pH 4 in various body organs and cell organelles (for example, the stomach and intracellular lysosomes). Commercial carbonation of drinks utilising pressure can obtain pH values of pH=2 to pH=3. The carbon dioxide dissolved in rain water results in a pH value of pH=5 to pH=6 depending on temperature.

The inventor considers that the bicarbonate ion produced by carbon dioxide in water can be considered as carbon dioxide hydroxide, $CO_2 \cdot OH^-$. That is, carbon dioxide in water can be viewed as an hydroxide ion carrier. The hydroxide ion per se is a relatively good electron donor but has slight reducing power. The oxidation of hydroxide ions can be represented by:

$$4OH^- \rightarrow O_2 + 2H_2O + 4e^- \quad E = -0.40\,V$$

When carbon dioxide in water is utilised to facilitate the electrolysis of water, the following reactions are considered to occur:

Cathode (reduction) $4H^+ + 4e^- \rightarrow 2H_2$

Anode (oxidation) $4OH^- \rightarrow O_2 + 2H_2O + 4e^-$ $4HCO_3^- \rightarrow 4OH^- + 4CO_2$ $2H_2O \rightarrow O_2 + 4H^+ + 4e^-$ In this scheme, hydrogen gas is produced at the cathode and oxygen gas is produced at the anode. Carbon dioxide gas is released from bicarbonate ions at the anode.

At low voltages, particularly at voltages below 1.23V, protons that are reduced to hydrogen at the cathode are thought to derive originally from the splitting of water by carbon dioxide as represented schematically above.

Thus a solution of carbon dioxide in water can be regarded as a catalyst or facilitator for the electrolysis of water. Carbon dioxide in water produces protons and bicarbonate ions in reasonable quantities under appropriate conditions of temperature and pressure. As a consequence, carbon dioxide in water decreases the power required for hydrogen production by electrolysis relative to standard electrolysis (where Power=Current×Voltage). Carbon dioxide decreases electrical resistance relative to standard electrolysis and this can be viewed as decreasing the reaction overpotential at the anode.

The carbon dioxide utilised to facilitate the electrolysis of water to produce hydrogen gas can be derived from the combustion of fossil fuels such as coal, oil and natural gas. The hydrogen gas produced from the electrolysis of water can be used in the Sabatier reaction to produce methane.

The enzyme carbonic anhydrase is the fastest biological enzyme known. Depending on the isoenzyme, each molecule of carbonic anhydrase is able to catalyse (hydrate) between 10,000 and 1,000,000 molecules of carbon dioxide per second. This enzyme speed becomes important at all levels of cell and organ physiology; from mitochondria to the lungs and kidneys. The proton concentration gradient that can arise from the action of carbonic anhydrase enzyme is transduced often into other forms of energy such as ATP concentrations and sodium and potassium gradients.

The inventor has hypothesised that the thermodynamics of carbon dioxide hydration per se may be as important as the kinetics of the carbonic anhydrase enzyme reaction. It therefore followed that one should concentrate carbon dioxide as much as possible in water in order to turn the resultant protons into hydrogen gas by electrolysis. The present specification illustrates this invention.

The above explanation of the invention is illustrated quantitatively in Example 1, Table 1.2, provided later in this specification. Thus at low potential (around 1 to 1.3 volts) the quantity of hydrogen produced is increased several hundred fold when carbon dioxide is added to water under pressure (1 atmosphere). All other results in other Examples substantiate this result.

Initially, experiments were conducted with sensitive analytical techniques such as gas chromatography, mass spectrometry and high-pressure liquid chromatography. These techniques were able to distinguish between hydrogen gas, methane, carbon monoxide, formic acid and oxalic acid. All these compounds are known, to a greater or lesser extent, to be the result of carbon dioxide in water reacting with hydrogen gas in the presence of electrons.

Later experiments were conducted using specific hydrogen detectors that are used in industry to detect hydrogen leaks in high pressure pipes. Three different hydrogen detectors were utilised. The disadvantage of these detectors is that they had to be calibrated by the manufacturer on a routine basis and they could not detect gases or compounds apart from hydrogen, methane and propane (when appropriately calibrated). One detector (the Sensit® HXG-3) was calibrated for hydrogen but also may have detected some methane. This detector was used initially to obtain results which were then repeated by other detectors. Mostly the detectors worked well in a linear manner up to about 10,000 ppm hydrogen.

EXAMPLES

Experiments were conducted utilising various carbon dioxide concentrations in water to facilitate the production of hydrogen gas by electrolysis. Carbon dioxide concentrations in water decreased the pH value of the water, i.e. carbon dioxide concentrations increased proton concentrations. The utilisation of carbon dioxide in water resulted in very significant increases in the production of hydrogen per unit of electricity relative to the absence of carbon dioxide.

Experiments were conducted using various carbon dioxide concentrations in sea water, saline waters and electrolyte solutions to facilitate the production of hydrogen gas. The utilisation of carbon dioxide in sea water, saline waters and electrolyte solutions resulted in very significant increases in the production of hydrogen per unit of electricity relative to the absence of carbon dioxide.

Experiments were conducted utilising a range of carbon dioxide concentrations in water, sea water and saline waters by altering pressure and temperature. Increasing the pressure of carbon dioxide in all waters increased the production of hydrogen very significantly. Decreasing temperature increased carbon dioxide solubility and increasing temperature increased carbon dioxide and water reactivity. In both cases, the production of hydrogen was increased significantly in all waters.

Experiments were conducted utilising carbon dioxide concentrations in water, sea water and saline waters with a range of low voltages and electrode materials. Significant hydrogen production was obtained in all waters at low voltages (less than 1.23V) utilising a range of electrode materials.

Example 1

Hydrogen Production from Water Under 1 Atmosphere $CO_2$ at Different Voltages

Figure 2:
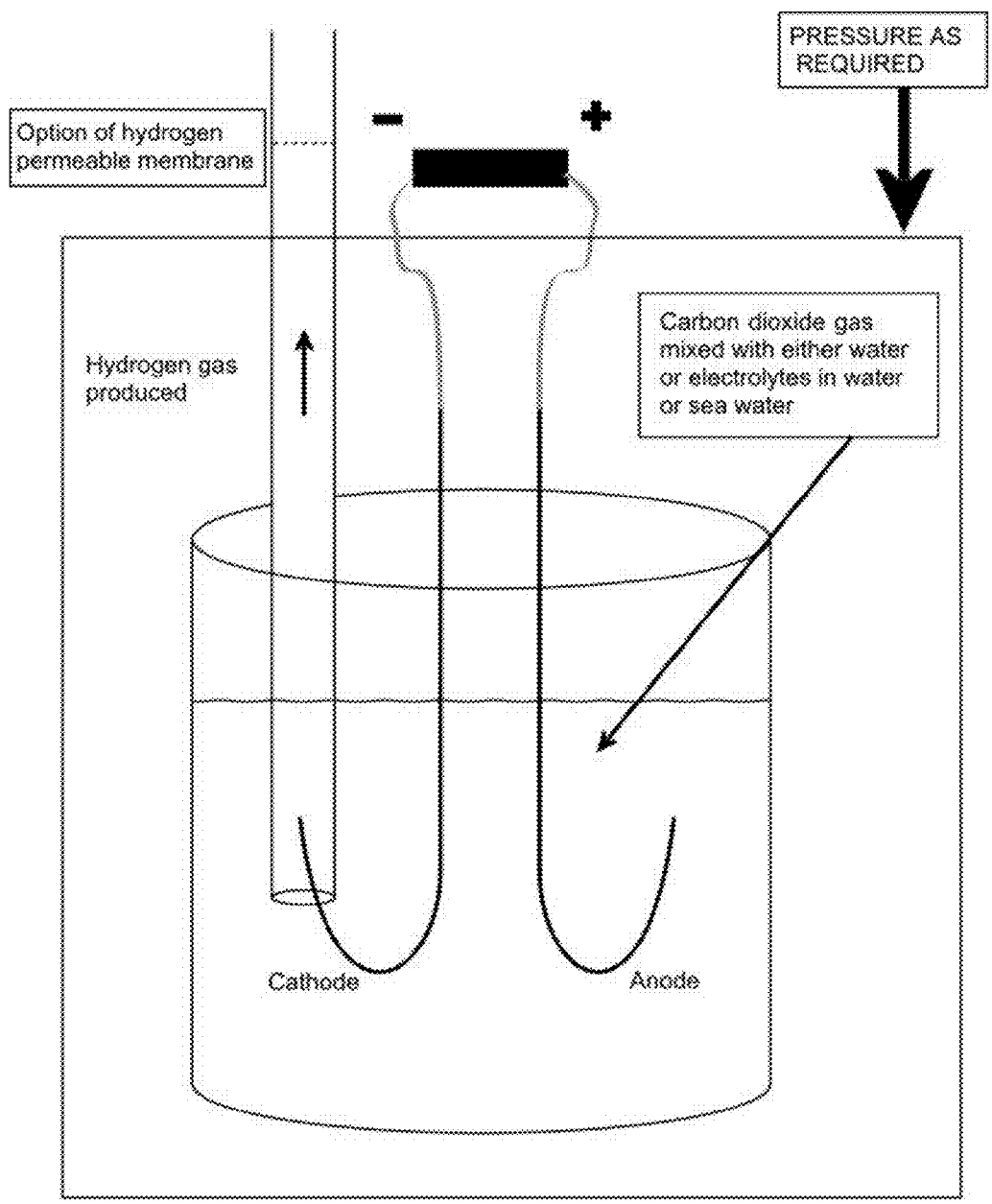
FIG. 2 is a diagrammatic representation of a modified Brownlee apparatus with platinum electrodes used in the Examples.
Figure 3:
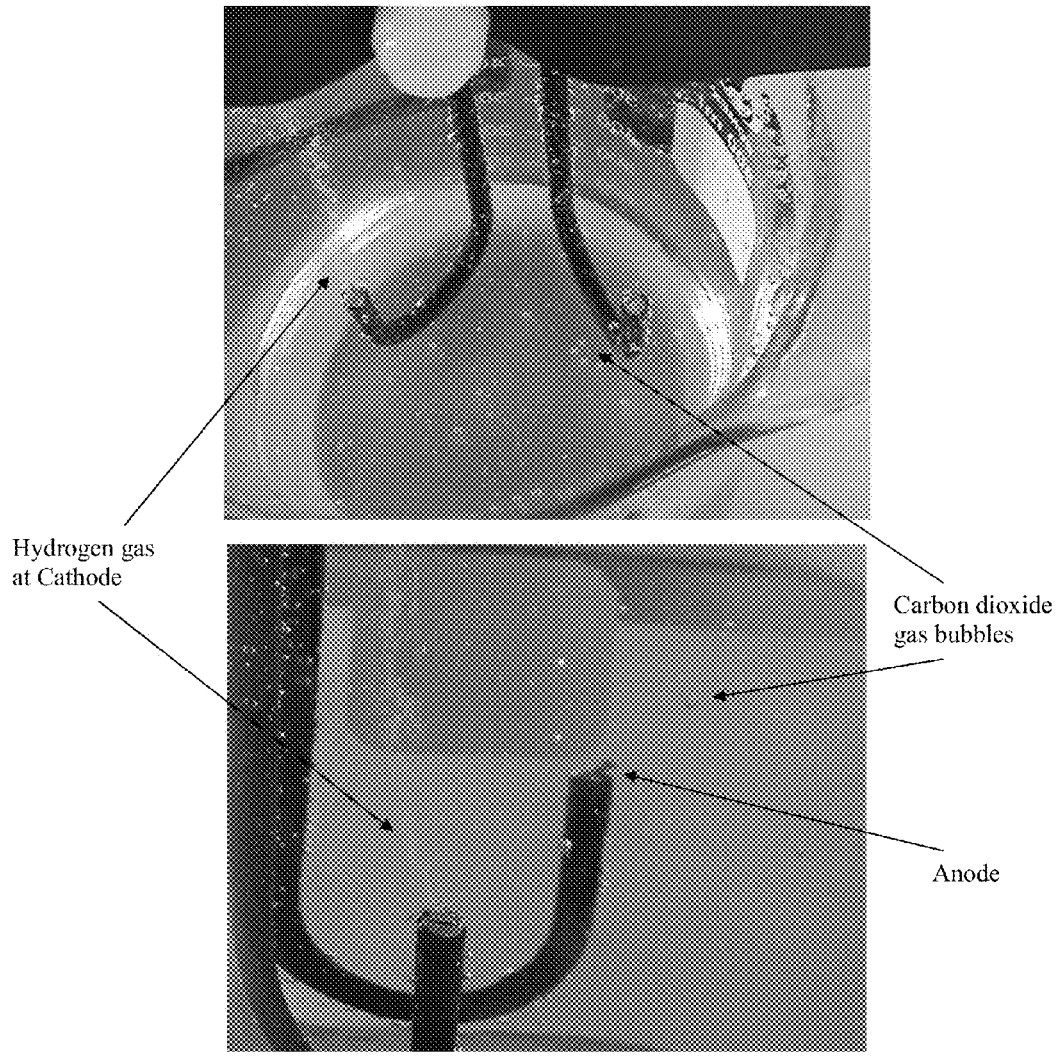
FIG. 3 shows photographs of hydrogen gas production from water with added carbon dioxide 1 atmosphere at low voltage in a modified Brownlee apparatus (temperature 10° C., <1 volt, platinum electrodes, pH of water 3.5). The absence of oxygen gas at the anode should be noted, and the distinct production of hydrogen gas at the cathode. This indicates that hydrogen production may occur at low voltage (less than 1.23 volts, the voltage required for the dissociation of water) from the reduction of protons that were produced from carbon dioxide molecules dissociating water molecules rather than the electrolysis of water per se.

This experiment was conducted at various voltages as shown in Tables 1.1 and 1.2, using current of less than 0.01 amps in a modified Brownlee or modified Hoffman apparatus (see FIGS. 1 and 2) with minimal platinum electrode surface area. Hydrogen gas was measured quantitatively as ppm hydrogen gas at 10 minutes following commencement of current flow.

TABLE 1.1

No voltage: control background reading (range over 10 measurements)

| WATER | NO VOLTAGE HYDROGEN PPM |
|---|---|
| WATER WITHOUT $CO_2$ ADDED | 0 to 10 |
| WATER WITH $CO_2$ ADDED 1 ATMOSPHERE | 50 to 100 |

The inventor hypothesises on the basis of the above data that the carbon dioxide used in the present experiments contained low levels of hydrogen. In order to control for this, the above data were subtracted from the data obtained when voltage was applied so as to determine the excess hydrogen evolved as a result of the electrolysis.

TABLE 1.2

Reading minus control background reading at 10 minutes (mean of 10 measurements)

| VOLTAGE (<0.01 amps) | WATER WITHOUT $CO_2$ ADDED Cathode Hydrogen ppm | WATER WITH $CO_2$ ADDED 1 ATMOSPHERE Cathode Hydrogen ppm |
|---|---|---|
| 1 volt | 0 | 400 |
| 1.3 volts | 10 | 530 |
| 5 volts | 50 | 1,450 |
| 10 volts | 320 | 2,550 |
| 20 volts | 1,080 | 3,970 |
| 30 volts | 2,980 | 4,960 |

The increase in hydrogen production from water with $CO_2$ added was significant compared to water without $CO_2$. Some methane may have been produced at the cathode. Oxygen was produced at the anode above 1.0 volt.

Example 2

Low Voltage Relative Hydrogen Production from Sea Water at $CO_2$ at 1 Atmosphere This experiment was conducted using various low voltages and current <0.01 amps. Hydrogen gas was measured quantitatively as ppm hydrogen gas in modified Brownlee and modified Hoffman apparatus at 3 minutes after commencement of current flow. Minimal platinum electrode surface area was used.

TABLE 2.1

No voltage
Control background reading (range over 10 measurements)

| SEA WATER | NO VOLTAGE HYDROGEN PPM |
|---|---|
| Sea water without $CO_2$ added | 0 to 10 |
| Sea water with $CO_2$ added 1 atmosphere | 50 to 100 |

TABLE 2.2

Reading minus control background reading at 3 minutes (mean of 10 measurements)

| VOLTAGE (<0.01 amps) | SEA WATER WITHOUT $CO_2$ ADDED Cathode Hydrogen ppm | SEA WATER WITH $CO_2$ ADDED 1 ATMOSPHERE Cathode Hydrogen ppm |
|---|---|---|
| 0.2 volt | 280 | 1,490 |
| 0.4 volt | 490 | 2,070 |
| 0.6 volt | 1,400 | 5,540 |
| 0.8 volt | 2,200 | 5,800 |
| 1.0 volt | 3,050 | 5,900 |

Increased hydrogen production at low voltages from sea water with $CO_2$ added was significant compared to sea water without $CO_2$. The hydrogen produced from sea water without added $CO_2$ may derive either from the inherent $CO_2$ present in sea water that originates from the atmosphere or from the reduction of cations to metals at the cathode which subsequently split water molecules.

Example 3

Low Voltage Relative Hydrogen Production from Electrolyte Solution at $CO_2$ 1 Atmosphere This experiment was conducted using 1.0M sodium chloride as electrolyte at various low voltages and current <0.01 amps. Hydrogen gas was measured quantitatively as ppm hydrogen gas in modified Brownlee and modified Hoffman apparatus at 3 minutes after commencement of current flow. Minimal platinum electrode surface area was used.

TABLE 3.1

No voltage
Control background reading (range over 10 measurements)

| ELECTROLYTE SOLUTION | NO VOLTAGE HYDROGEN PPM |
|---|---|
| Electrolyte solution without $CO_2$ added | 0 to 10 |
| Electrolyte solution with $CO_2$ added 1 atmosphere | 50 to 100 |

TABLE 3.2

Reading minus control background reading at 3 minutes (mean of 10 measurements)

| VOLTAGE (<0.01 amps) | ELECTROLYTE SOLUTION WITHOUT $CO_2$ ADDED Cathode Hydrogen ppm | ELECTROLYTE SOLUTION WITH $CO_2$ ADDED 1 ATMOSPHERE Cathode Hydrogen ppm |
|---|---|---|
| 0.2 volt | 190 | 900 |
| 0.4 volt | 450 | 1,800 |
| 0.6 volt | 800 | 2,700 |
| 0.8 volt | 1,400 | 4,300 |
| 1.0 volt | 2,100 | 6,200 |
| 5.0 volts (0.02 amps) | 7,800 | 11,300 |

Increased hydrogen production at low voltages from electrolyte solution with $CO_2$ added was significant compared to electrolyte solution without $CO_2$. The hydrogen production from electrolyte solution without $CO_2$ added may derive from the reduction of cations to metals at the cathode which subsequently split water molecules. Some methane may have been produced at the cathode. Oxygen was produced at the anode above 1.0 volt.

Example 4

Relative Hydrogen Production from Water at Various $CO_2$ Pressures

This experiment was conducted at voltage 5V and current <0.01 amps. Hydrogen gas was measured quantitatively as ppm hydrogen gas in modified Brownlee and modified Hoffman apparatus at 10 minutes. Minimal platinum electrode surface area was used.

TABLE 4.1

Hydrogen production at 10 minutes (mean of 10 measurements)

| $CO_2$ ATMOSPHERES | WATER WITH $CO_2$ ADDED Cathode Hydrogen ppm |
|---|---|
| 1 | 1,400 |
| 2 | 2,100 |
| 3 | 3,300 |
| 5 | 4,300 |
| 10 | 6,800 |
| 20 | 8,200 |

Increased hydrogen production with increased $CO_2$ pressures was significant. Oxygen was produced at the anode.

The invention claimed is:

1. A process for generating hydrogen, said process comprising the steps of:
   a) exposing an aqueous liquid to a gas containing carbon dioxide; and
   b) passing a current through the aqueous liquid so as to generate hydrogen;
   wherein the aqueous liquid has no electrolyte other than an electrolyte derived from splitting of water by the carbon dioxide.

2. The process of claim 1 wherein step a) comprises either passing a gas containing carbon dioxide through the aqueous liquid or exposing the surface of the aqueous liquid to a gas containing carbon dioxide or both.

3. The process of claim 2 wherein the gas is released to the atmosphere following step a) whereby the process is a process for reduction of emissions of carbon dioxide into the atmosphere.

4. The process of claim 3 wherein the gas in step a) is a waste gas from an industrial process.

5. The process of claim 1 wherein step a) comprises exposing the aqueous liquid to a gas containing carbon dioxide, said carbon dioxide having a partial pressure in said gas of at least about 0.01 atmospheres.

6. The process of claim 5 wherein the gas comprises at least about 95% carbon dioxide on a volume basis.

7. The process of claim 1 wherein the current is applied at a voltage of about 0.1 to about 50V.

8. The process of claim 7 wherein the voltage is less than about 1.3V.

9. The process of claim 1 wherein step b) comprises passing a current through the aqueous liquid between an anode and a cathode and is conducted at a voltage of about 0.4 to about 4V, whereby the process produces oxygen at the anode.

10. The process of claim 9 additionally comprising using the oxygen in Oxyfuel combustion.

11. The process of claim 1 wherein the current is less than about 20 amps.

12. The process of claim 1 wherein step b) comprises applying a voltage between a cathode and an anode, wherein the cathode is at least partially immersed in the aqueous liquid and the anode is in electrical communication with the aqueous liquid.

13. The process of claim 1 wherein hydrogen evolved in said process is at least partially purified by passing through a gas separation membrane.

14. The process of claim 1 additionally comprising:
   c) reacting the hydrogen with carbon dioxide so as to produce methane and water.

15. The process of claim 1 wherein the carbon dioxide is derived from the combustion of a fossil fuel.

16. The process of claim 1 wherein the process is conducted in an electrolyser comprising a proton exchange membrane or a polymer electrolyte membrane (PEM).

17. A method of producing methane and water comprising:
   a) exposing an aqueous liquid to a gas containing carbon dioxide; and
   b) passing a current through the aqueous liquid so as to generate hydrogen; and
   c) reacting the hydrogen with carbon dioxide so as to produce methane and water;
   wherein the aqueous liquid has no electrolyte other than an electrolyte derived from splitting of water by the carbon dioxide.

18. A method for increasing the rate of hydrogen production in the electrolysis of an aqueous solution, said method comprising exposing the aqueous solution to a gas containing carbon dioxide prior to and/or during said electrolysis;
   wherein the aqueous liquid has no electrolyte other than an electrolyte derived from splitting of water by the carbon dioxide.

19. The method of claim 18 wherein the carbon dioxide is, or is derived from, an industrial waste gas.

20. The process of claim 1 wherein the gas in step a) is at a pressure of about 2 to 100 atmospheres.

21. The process of claim 1 wherein the aqueous liquid is at a temperature of less than about 15° C.

* * * * *